United States Patent
Smits et al.

(10) Patent No.: US 9,892,612 B2
(45) Date of Patent: Feb. 13, 2018

(54) METHOD FOR RESPONDING TO A DETECTED FALL AND AN APPARATUS FOR IMPLEMENTING THE SAME

(71) Applicant: KONINKLIJKE PHILIPS N.V., Eindhoven (NL)

(72) Inventors: Tine Smits, Beerse (BE); Heribert Baldus, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/106,065

(22) PCT Filed: Dec. 17, 2014

(86) PCT No.: PCT/EP2014/078103
§ 371 (c)(1),
(2) Date: Jun. 17, 2016

(87) PCT Pub. No.: WO2015/091581
PCT Pub. Date: Jun. 25, 2015

(65) Prior Publication Data
US 2016/0321903 A1  Nov. 3, 2016

(30) Foreign Application Priority Data

Dec. 20, 2013 (EP) ................... 13198944

(51) Int. Cl.
| | | |
|---|---|---|
| G08B 23/00 | (2006.01) | |
| G08B 21/04 | (2006.01) | |
| G06F 19/00 | (2011.01) | |
| G08B 25/01 | (2006.01) | |

(52) U.S. Cl.
CPC ..... *G08B 21/0446* (2013.01); *G06F 19/3418* (2013.01); *G08B 25/016* (2013.01)

(58) Field of Classification Search
None
See application file for complete search history.

(56) References Cited

U.S. PATENT DOCUMENTS

| | | | |
|---|---|---|---|
| 6,221,010 B1 * | 4/2001 | Lucas | A61B 5/0008 600/300 |
| 7,248,172 B2 | 7/2007 | Clifford et al. | |
| 8,508,372 B2 | 8/2013 | Cuddihy | |
| 8,531,291 B2 | 9/2013 | Tran | |
| 2004/0212505 A1 * | 10/2004 | Dewing | A61B 5/0002 340/573.1 |
| 2011/0205053 A1 | 8/2011 | Chen et al. | |
| 2014/0062702 A1 * | 3/2014 | Rubio Andres | G08B 21/043 340/573.1 |
| 2014/0191863 A1 * | 7/2014 | Ten Kate | A61B 5/1116 340/539.12 |

FOREIGN PATENT DOCUMENTS

| | | |
|---|---|---|
| WO | 2004114245 A1 | 12/2004 |
| WO | 2010004538 A1 | 1/2010 |
| WO | 2011055255 A1 | 5/2011 |
| WO | 2012146957 A1 | 11/2012 |

* cited by examiner

*Primary Examiner* — Joseph Feild
*Assistant Examiner* — John Mortell

(57) ABSTRACT

There is provided a method of responding to a detected fall, the method comprising determining which one or two or more actions to perform in response to detecting a fall by a user based on a user profile and/or user preference and/or the context of the detected fall; and performing the determined action.

18 Claims, 7 Drawing Sheets

METHOD FOR RESPONDING TO A DETECTED FALL AND AN APPARATUS FOR IMPLEMENTING THE SAME

CROSS-REFERENCE TO PRIOR APPLICATIONS

This application is the U.S. National Phase application under 35 U.S.C. §371 of International Application No. PCT/EP2014/078103, filed on Dec. 17, 2014, which claims the benefit of European Patent Application No. 13198944.4, filed on Dec. 20, 2013. These applications are hereby incorporated by reference in their entirety herein.

TECHNICAL FIELD OF THE INVENTION

The invention relates to systems for detecting a fall by a user, and in particular relates to a method and apparatus for determining a follow-up action to take when a fall is detected.

BACKGROUND TO THE INVENTION

Falls affect millions of people each year and result in significant injuries, particularly among the elderly. In fact, it has been estimated that falls are one of the top three causes of death in elderly people. A fall is defined as a sudden, uncontrolled and unintentional downward displacement of the body to the ground, followed by an impact, after which the body stays down on the ground.

A personal emergency response system (PERS) is a system in which help can be assured. By means of Personal Help Buttons (PHBs) the user can push the button to summon help in an emergency. A majority of calls are because the user has fallen. Also, if the user suffers a severe fall (for example by which they get confused or even worse if they are knocked unconscious), the user might be unable to push the button, which might mean that help doesn't arrive for a significant period of time, particularly if the user lives alone. The consequences of a fall can become more severe if the user stays lying for a long time.

Fall detection systems are also available that process the output of one or more movement sensors to determine if the user has suffered a fall. Most existing body-worn fall detection systems make use of an accelerometer (usually an accelerometer that measures acceleration in three dimensions) and they are configured to infer the occurrence of a fall by processing the time series generated by the accelerometer. Some fall detection systems can also include an air pressure sensor, for example as described in WO 2004/114245, for measuring the height, height change or absolute altitude of the fall detection system.

In general, a fall detector tests on features like impact, orientation, orientation change, height change, vertical velocity, and alike. Reliable detection results when the set of computed values for these features is different for falls than for other movements that are not a fall.

Typically, when a fall is detected by the fall detection system, an alarm signal is transmitted to a remote call centre, from where an operator can arrange for assistance (e.g. the emergency services, a care provider or a family member) to be sent to the user. In other cases, if the fall detection system is provided with suitable communications functionality, the fall detection system can contact the emergency services, a care provider or a family member directly.

In some cases a revocation period is applied when a fall is detected which allows a short period (e.g. 1 minute) for a user to stand up after a fall has occurred (and been detected by the fall detection system) before the alarm is triggered or sent to the remote call centre.

SUMMARY OF THE INVENTION

Currently, when a fall is detected by a fall detection system, the procedures followed by the fall detection system and the personnel at the remote call centre are the same for each user and for each fall. That is, if a revocation period is used by the system, the same revocation period is applied to a fall regardless of the severity or context of the detected fall. The triggering of an alarm (e.g. the sending of the alarm signal to the remote call centre or the initiation of a call to a family member/call provider or emergency services) after a fall also does not take into account any particular user preferences or the severity or context of the fall.

Thus, the invention aims to address these deficiencies with current fall detection systems by customising or tailoring the follow-up action to a detected fall according to a user profile and/or user preference and/or the context of the detected fall.

According to a first aspect, there is provided a method of responding to a detected fall, the method comprising determining an action to perform in response to detecting a fall by a user based on a user profile and/or user preference and/or the context of the detected fall; and performing the determined action.

In some embodiments the action is determined from a set comprising two or more of: taking no action, requesting help for the user, initiating a call, waiting for the expiry of a revocation period before requesting help for the user or initiating a call, and checking a status of the user after another revocation period.

In some embodiments the user profile comprises information on whether the user lives alone, the fall risk of the user and/or the fall history of the user.

In some embodiments the user preference comprises an indication of the length of a revocation period after the detection of the fall before help is requested for the user or a call is initiated.

In some embodiments the context of the detected fall comprises an indication of when the detected fall occurred, the location of the user when the detected fall occurred, the environmental temperature, the magnitude of a detected impact and/or the direction that the user fell.

In some embodiments the step of determining further comprises determining the action to perform based on a status of the user following the fall.

In some embodiments the status of the user comprises an amount of movement by the user following the detected fall, an indication of whether the user has stood up following the detected fall and/or measurements of physiological characteristics.

In some embodiments the step of determining comprises determining whether the detected fall has occurred indoors or outdoors; determining that help should be requested for the user or a call initiated if the detected fall is determined to have occurred outdoors; and determining that a revocation period should expire before help is requested for the user or a call initiated if the detected fall is determined to have occurred indoors.

In other embodiments the step of determining comprises determining whether the temperature in the environment in which the detected fall has occurred is below a threshold; determining that help should be requested for the user or a call initiated if the temperature in the environment is below the threshold; and determining that a revocation period should expire before help is requested for the user or a call initiated if the temperature in the environment is above the threshold.

In other embodiments the step of determining comprises determining whether the user lives alone from a user profile; determining that help should be requested for the user or a call initiated if the user lives alone; and determining that a revocation period should expire before help is requested for the user or a call initiated if the user does not live alone.

According to a second aspect, there is provided a computer program product having computer readable code embodied therein, the computer readable code being configured such that, on execution by a processing unit, the processing unit performs any of the methods described above.

According to a third aspect, there is provided an apparatus for providing a response to a detected fall, the apparatus comprising a processing unit configured to determine an action to perform in response to detecting a fall by a user based on a user profile and/or user preference and/or the context of the detected fall; and perform the determined action.

In some embodiments the action comprises one of: taking no action, requesting help for the user, initiating a call, waiting for the expiry of a revocation period before requesting help for the user or initiating a call, and checking a status of the user after another revocation period.

In some embodiments the processing unit is configured to obtain the user profile and/or user preference from a memory.

In some embodiments the processing unit is configured to obtain information on the context of the detected fall from one or more sensors.

In some embodiments the user profile comprises information on whether the user lives alone, the fall risk of the user and/or the fall history of the user.

In some embodiments the user preference comprises an indication of the length of a revocation period after the detection of the fall before help is requested for the user or a call is initiated.

In some embodiments the context of the detected fall comprises an indication of when the detected fall occurred, the location of the user when the detected fall occurred, the environmental temperature, the magnitude of a detected impact and/or the direction that the user fell.

In some embodiments the processing unit is configured to determine the action to perform based on a status of the user following the fall.

In some embodiments the status of the user comprises an amount of movement by the user following the detected fall, an indication of whether the user has stood up following the detected fall and/or measurements of physiological characteristics.

In some embodiments the processing unit is configured to determine an action to perform by determining whether the detected fall has occurred indoors or outdoors; determining that help should be requested for the user or a call initiated if the detected fall is determined to have occurred indoors; and determining that a revocation period should expire before help is requested for the user or a call initiated if the detected fall is determined to have occurred outdoors.

In other embodiments the processing unit is configured to determine an action to perform by determining whether the temperature in the environment in which the detected fall has occurred is below a threshold; determining that help should be requested for the user or a call initiated if the temperature in the environment is below the threshold; and determining that a revocation period should expire before help is requested for the user or a call initiated if the temperature in the environment is above the threshold.

In other embodiments the processing unit is configured to determine an action to perform by determining whether the user lives alone from a user profile; determining that help should be requested for the user or a call initiated if the user lives alone; and determining that a revocation period should expire before help is requested for the user or a call initiated if the user does not live alone.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1A:
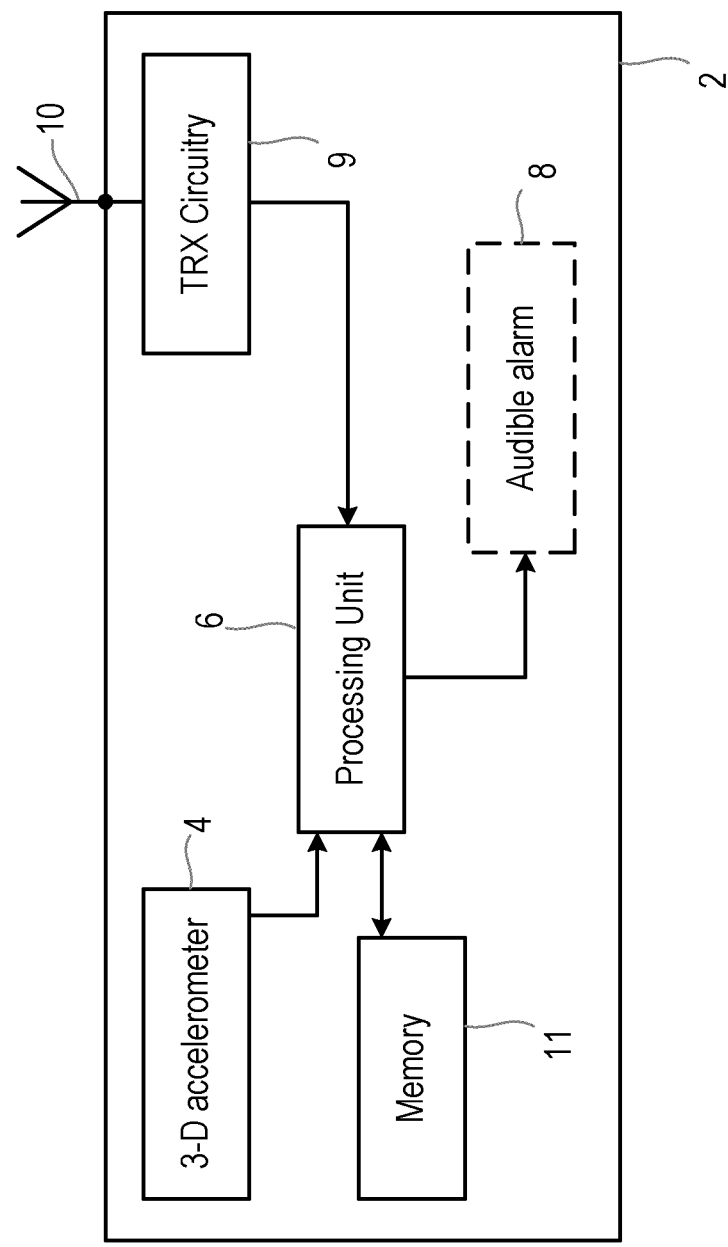
FIG. 1(a) shows an exemplary fall detection system in which the invention can be implemented.

FIG. 1(a) illustrates an exemplary fall detection device 2 that in some embodiments can implement a method in accordance with the invention. The device 2 is in the form of a sensor unit that is to be worn by a user. The device 2 can be provided in the form of a pendant with a neck cord for placement around the user's neck, but alternatively the device 2 can be configured to be worn at or on a different part of the user's body, such as the wrist, waist, trunk, pelvis or sternum, and will comprise a suitable arrangement for attaching the device 2 to that part of the body (for example a belt or a strap).

The device 2 is used to measure the accelerations experienced by the user and to process the measurements to determine the vertical velocity and then the change in height of the device 2 (and hence the change in height of the user). Although not described herein, it will be appreciated that a device 2 may perform additional processing on the acceleration measurements to identify other characteristics of a fall, such as an impact or a period of immobility following an impact. It will also be appreciated that the device 2 may contain further sensors, such as a gyroscope, magnetometer, air pressure sensor and/or air flow sensor, whose signals can be processed to determine, or to assist in determining, height, orientation or other characteristics associated with a fall.

The device 2 comprises an accelerometer 4 that measures acceleration along three orthogonal axes. The signals output by the accelerometer 4 are provided to a processing unit 6 for analysis. As illustrated, the device 2 comprises an audible alarm unit 8 that can be triggered by the processing unit 6 if a fall is detected. This alarm can summon help to the user. However, it will be appreciated that the presence of an audible alarm unit in the device 2 is optional. A further optional component is a help button that can be pressed by a user to summon help, in which case a call is placed to a remote call centre.

The device 2 further comprises transmitter or transceiver circuitry 9 and associated antenna 10 that can be used for transmitting the results of the processing (e.g. an alarm signal indicating that a fall has been detected) to a remote (base) unit or for placing an emergency call to a call centre to summon help in the event that a fall is detected or in the event that a help button (if present) has been pressed. Where the transmitter or transceiver circuitry 9 is configured to communicate with a base station, the circuitry 9 may be configured according to any known wireless technology, for example Wi-Fi, Bluetooth, Near Field Communication (NFC), etc. Where the transmitter or transceiver circuitry 9 is also or alternatively provided to enable communications with a public telephone network, such as a mobile telephone network, the circuitry 9 may be also or alternatively configured for use with any suitable type of second-, third- or fourth-generation communication network, including GSM, WCDMA, LTE, etc.

The device 2 also optionally comprises a memory 11 that is used for storing measurements from the accelerometer 4, and for storing the results of the processing by the processing unit 6. In some embodiments, the memory 11 can be used to store information on a user profile and/or user preferences (as described in more detail below). The memory 11 can also be used to store computer readable code for execution by the processing unit 6 to enable the processing unit 6 to determine whether a fall has taken place and/or to execute methods according to the invention.

In some embodiments, the accelerometer 4 is a micro-electromechanical system (MEMS) accelerometer.

The acceleration experienced by the accelerometer 4 can be sampled at a rate of 30 Hz, although it will be appreciated that many other sampling frequencies can be used (for example 50 Hz).

Figure 1B:
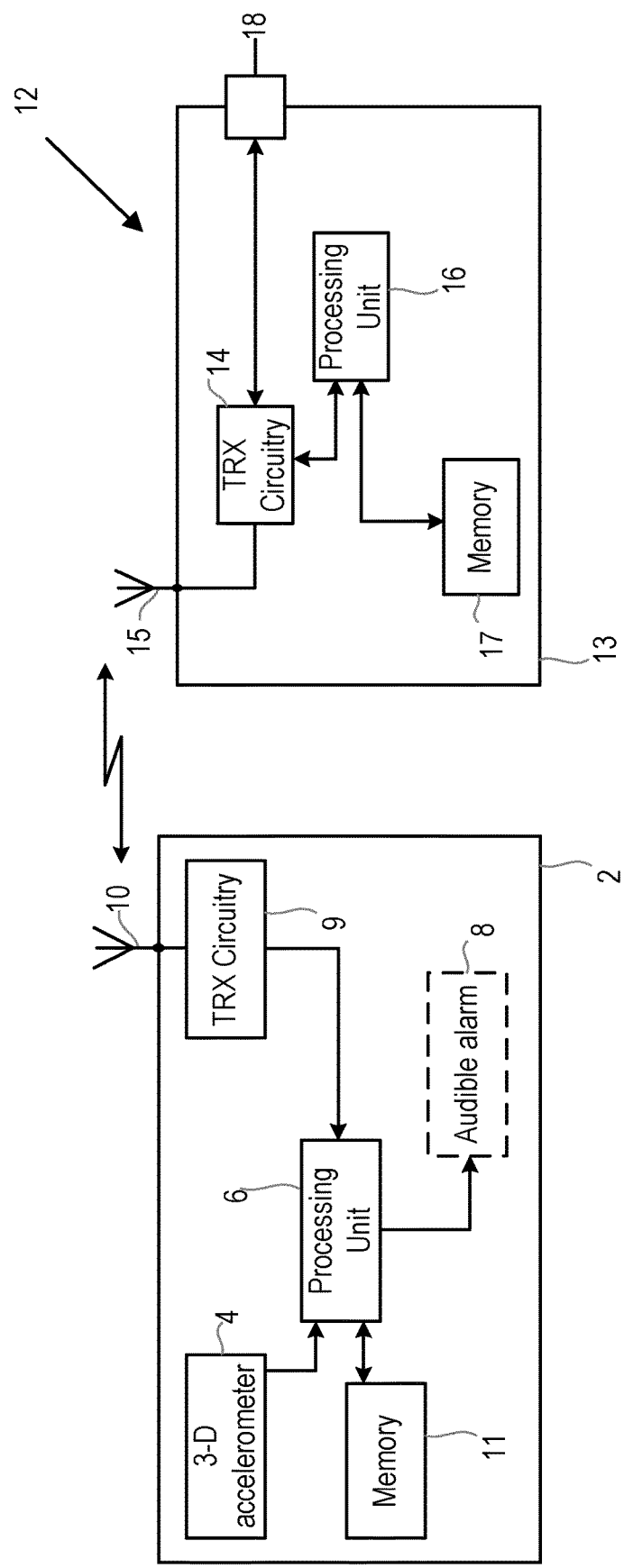
FIG. 1(b) shows an alternative exemplary fall detection system in which the invention can be implemented.

In an alternative embodiment, the invention can be implemented in a system 12 as illustrated in FIG. 1(*b*). In this embodiment, the user-worn device 2 is part of a system 12 in which the processing of the accelerometer measurements can be performed in a base unit 13 that is separate to the device 2 worn by the user. In that case, the accelerometer measurements can be transmitted from the device/sensor unit 2 to the base unit 13 via the transceiver circuitry 9.

The base unit 13 comprises transceiver circuitry 14 and antenna 15 for receiving transmissions (such as the accelerometer measurements) from the device 2 and a processing unit 16.

The base unit 13 also optionally comprises a memory 17 that is used for storing accelerometer measurements received from the device 2, and for storing the results of the processing by the processing unit 16. In some embodiments, the memory 17 can be used to store information on a user profile and/or user preferences (as described in more detail below). The memory 17 can also be used to store computer readable code for execution by the processing unit 16 to enable the processing unit 16 to determine whether a fall has taken place and/or to execute methods according to the invention.

The transceiver circuitry 14 may be configured for wirelessly placing an emergency call to a call centre, and/or may be configured for connection to a conventional public switched telephone network (PSTN) line via port 18.

In a further alternative, the device 2 may perform some of the initial processing steps on the accelerometer measurements before transmitting the results to the base unit 13 which, for example, completes the processing and estimates the vertical velocity and change in height of the device 2.

It will be appreciated that only components of the device 2 (and system 12) that are required for explaining the invention have been illustrated in FIGS. 1(*a*) and (*b*), and a device 2 (or system 12) that can implement the invention may include further components and functionality to those described herein. For example, it will be appreciated that a device 2 (and base unit 13) will include some form of power source or supply and circuitry for controlling the operation of the device 2 (and base unit 13). Also, the device 2 may comprise a loudspeaker and/or microphone for enabling a user to communicate with the remote call centre or the emergency services. In addition, the fall detection system 2 may comprise a satellite positioning system (SPS) receiver, such as a Global Positioning System (GPS) receiver, for tracking the location of the device 2. Information on the location of the device 2 can be transmitted to the call centre in the event that an alarm is triggered to enable help or assistance to be sent to the right location.

Figure 2:
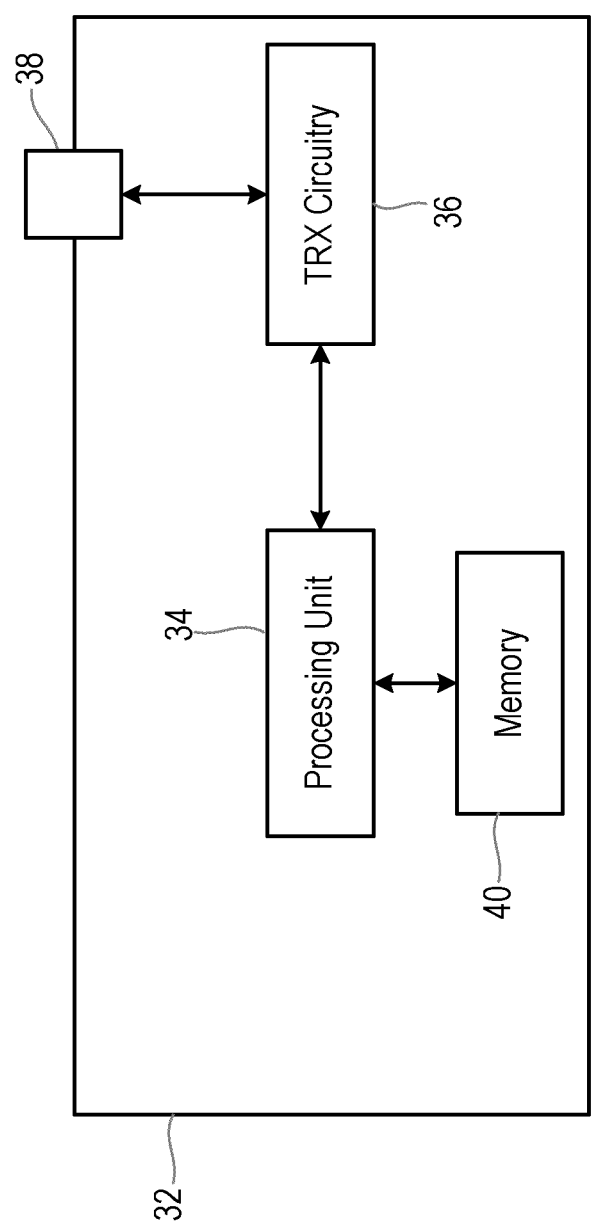
FIG. 2 is a block diagram of a system that can be used in a remote call centre in which embodiments of the invention can be implemented.

FIG. 2 shows a block diagram of a system 32 that can be provided in a remote call centre for receiving alarm signals from fall detection devices 2 or systems 12. The system 32 comprises a processing unit 34 that processes received alarm signals and that initiates calls in order to get help to a user that has suffered a fall. The system 32 also includes transceiver circuitry 36 and port 38 for allowing the system 32 to communicate with the devices 2 or systems 12 and to initiate calls to obtain help for the user.

The system 32 also optionally comprises a memory 40 that can be used for storing measurements from the accelerometer 4 (for example in case the information is useful for validating or testing the fall detection algorithm used by the device 2 or system 12), and/or information required for establishing a call to obtain assistance for a user (for example the telephone number of a family member or a care provider) and/or, in some embodiments, information on a user profile and/or user preferences (as described in more detail below), The memory 40 can also be used to store computer readable code for execution by the processing unit 34 to enable the processing unit 34 to execute methods according to the invention.

The system 32 may also include components that enable a call operator at the remote call centre to interact with the user when an alarm signal is received (for example to check if the user is okay after the detected fall and/or to reassure the user that assistance is on its way) and also to interact with the family member, care provider and/or emergency services when they are called.

A fall can be broadly characterised by, for example, a change in altitude of around 0.5 to 1.5 meters (the range may be different depending on the part of the body that the device 2 is to be worn and the height of the user), culminating in a significant impact, followed by a period in which the user does not move very much. Thus, in a fall detection algorithm as described above, movement sensor measurements can be processed to extract values for one or more features including a change (specifically a reduction) in height/altitude (which is usually derived from measurements from an air pressure sensor, but can also or alternatively be derived from the measurements from the accelerometer 4, for example if the air pressure sensor is omitted), a maximum activity level (i.e. an impact) around the time that the change in altitude occurs (typically derived from the measurements from the accelerometer 4), a period in which the user is relatively inactive following the impact (again typically derived from the measurements from the accelerometer 4), the vertical velocity, the occurrence of free fall (typically derived from measurements from the accelerometer 4), a change in orientation upon falling (typically derived from the measurements from the accelerometer 4 or from a gyroscope, if present) and an indication of a height/altitude increase after a detected impact.

Algorithms for detecting a fall using measurements from an accelerometer 4 and optionally other sensors are known in the art and will not be described in detail herein.

As noted above, conventionally when a fall is detected by a fall detection system, the procedures followed by the fall detection system and the personnel at the remote call centre are the same for each user and for each fall.

In some typical systems, an alarm signal is sent to the remote call centre by the device 2 or system 12 when a fall by the user is detected. This alarm signal is logged or registered at the call centre. Some systems are configured to summon help for the user straight away (for example by calling a family member, care provider or the emergency services), while other systems are configured to wait for a predetermined period (known as a "revocation period") before summoning help for the user. In some systems, the device 2 or system 12 is configured to apply the revocation period before sending the alarm signal to the remote call centre. In those systems, after detecting a fall by the user, the device 2 or system 12 waits for the preset revocation period before sending the alarm signal to the remote call centre, which then acts on the signal to summon help for the user straight away. If the device 2 or system 12 detects that the user has got up or has otherwise cancelled the issue of an alarm signal (for example by pressing a button on the device 2) before the expiry of the revocation period, then the alarm signal is not sent to the remote call centre.

In each of the above cases, if a revocation period is used by the system, the same revocation period is applied to a fall regardless of the severity or context of the detected fall. If a revocation period is not used by the system, this is again the case for all users, regardless of the severity or context of the detected fall. The timing of the triggering of an alarm (e.g. the sending of the alarm signal to the remote call centre or the initiation of a call to a family member/call provider or emergency services) after a fall also does not take into account any particular user preferences or profile of the user.

The invention addresses this problem by taking into account a user profile and/or user preference and/or the context of the detected fall when determining an action to take in response to a fall by the user being detected. In some embodiments the method, or part of the method, can be applied in the device 2 or system 12, in which case the alarm signal sent by the device 2 or system 12 to the call centre may indicate the determined action or the result of evaluating the user profile, user preference and/or the fall context (in which case a system in the call centre determines the appropriate action to take). In other embodiments, the method can be implemented in a system 32 at the remote call centre, in which case the device 2 or system 12 sends an alarm signal as soon as a fall is detected, and the system 32 in the remote call centre determines the action to take. The set of possible actions that can be taken can comprise any of: taking no action (i.e. ignoring the detected fall/alarm signal), sending out an alarm to request help for the user, informing a care provider or family member that the user has fallen, waiting for a revocation period, waiting for a revocation period of a specific length, or checking the status of the user again after another (or longer) revocation period.

Figure 3:
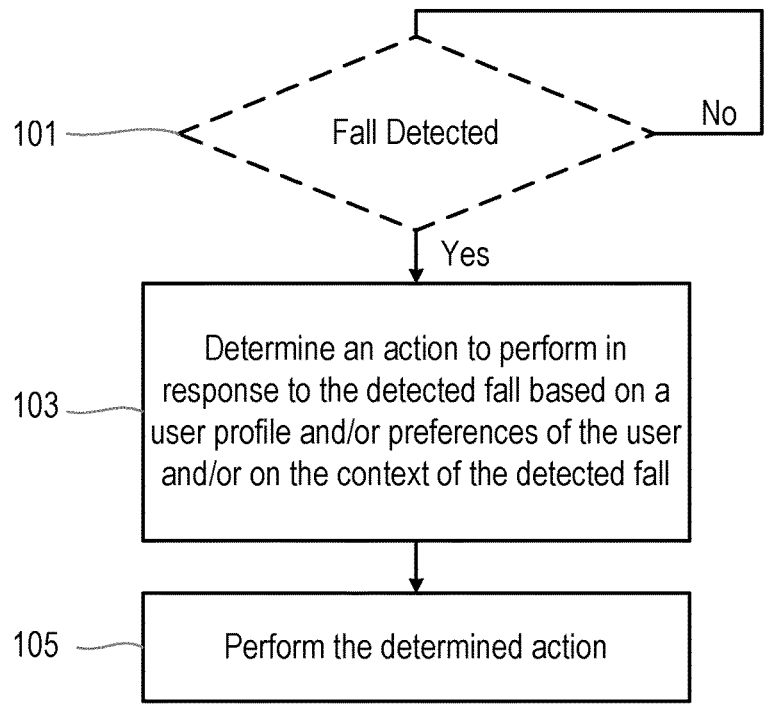
FIG. 3 is a flow chart illustrating a general method according to the invention.

The flow chart in FIG. 3 illustrates a general method in accordance with the invention. In a first step, step 101, it is determined whether a fall is detected. When a fall has been detected, the method moves to step 103 in which an action to perform in response to the detected fall is determined based on a user profile and/or preferences of the user and/or on the context of the detected fall. In step 103, it is preferably determined which one of two or more actions is to be performed in response to the detected fall. Thus step 103 provides that the user profile and/or user preference and/or the context of the detected fall is used to determine which action (and preferably which one of two or more available actions) is to be performed in response to the detected fall. Once the action has been determined in step 103, the method comprises performing the determined action (step 105).

The user profile can comprise information about the user such as their living conditions (e.g. whether they live alone or with at least one other person), their fall risk (e.g. high, medium, low), their fall history. The user profile can be stored in a memory 11, 17, 40 of the device/system performing the method. A user that does not live alone may have people nearby that can come to their aid when they have suffered a fall so assistance provided via the fall detection device 2 or system 12 may not be required immediately. A user with a high fall risk and/or one or more recent falls in their fall history may require assistance more quickly than a user with a low fall risk and/or no recent falls.

The user preference can comprise information on the user's preference for being contacted after a fall. Every user is different. Some users prefer to be contacted or checked on immediately when a fall is detected. Other users prefer to feel like they are in charge of the situation and only want to be contacted when it is really necessary. The user preference information can therefore indicate a user's preference on how long the revocation period should be after a fall is detected before some assistance is sought for the user, Thus, the preference information could indicate that there should be no revocation period, a revocation period of a standard or default length, or a shorter or longer revocation period of a user-specified length. The user preferences can be stored in a memory 11, 17, 40 of the device/system performing the method.

The context of the fall can provide an indication of how severe the fall was and/or how urgently the user might need assistance. Falls can be more dangerous in different situations. For example, a fall in winter time, a fall at night or a fall outdoors (or a combination of these) might suggest that the fall is more severe and the user may require assistance more urgently (in which case a revocation period (if set) can be ignored and assistance obtained immediately). On the other hand, a fall during the summer, a fall during the day or a fall indoors might not be so severe and the revocation period could be allowed to expire before requesting assistance for the user. In addition, if a user is immobile following a fall, there may be a risk of hypothermia, particularly if the temperature in the environment is low or substantially below normal room temperature (with normal room temperature being around 21° C.). Therefore, if the environmental temperature is low, e.g. below a threshold (which can be set at a temperature that is a number of degrees below room temperature, for example, 1-5° C. below normal room temperature) then the user may require assistance more urgently and a revocation period can be ignored or skipped. If the environmental temperature is above the threshold temperature then a revocation period can be allowed to expire before requesting assistance for the user. The context information can therefore indicate the location of the detected fall (e.g. indoors/outdoors, or a specific location), the time of the detected fall (e.g. day/night, or a specific time), the temperature in the environment (e.g. warm/cold, or a specific temperature) and/or the date. It will be appreciated that the temperature information can be used to provide an indication on the season in which the fall has taken place, and/or whether the fall has taken place indoors or outdoors.

Other context information that can provide an indication of how severe the fall was includes information about the fall itself, such as the magnitude of the impact and/or the direction in which the fall has occurred (for example the user has fallen forwards, backwards, sideways, etc.).

It will be appreciated that in embodiments in which information on the context of the fall is used, suitable additional sensors or processing are provided in the device 2 or system 12 (as appropriate) in order to collect that context information. For example, where the context information comprises the location of the fall, the device 2 can be provided with some means for detecting the location of the user, such as an SPS receiver or some means for detecting the location of the user in an indoor environment.

Where the context information comprises the time and/or date of the detected fall, the processing unit 6, 16 in the device 2 or system 12 can monitor the current time and/or date. Where the context information comprises the temperature of the environment around the user, the device 2 can comprise a temperature sensor for sensing the environmental temperature.

Where the context information provides an indication of how severe the fall was, the processing unit 6, 16 that evaluates the accelerometer data to determine if a fall has occurred can also evaluate the accelerometer data (and other sensor data if other sensors are present in the device 2) to determine the severity of the fall, such as the direction of the fall and/or the magnitude of the impact with the ground (e.g. the magnitude of the or a peak or the highest peak in the accelerometer data).

It will be appreciated that step 103 can comprise determining the action to perform based on multiple ones of the user profile, user preferences and context information.

In addition to the above user profile, user preference and/or information on the context of the fall, information on the status of the user following the fall can be evaluated in step 103 to determine the follow-up action. Information on the status of the user can include the amount of movement by the user following the detected fall, whether or not the user has stood up again following the fall (indicating that the alarm may have been revoked) and/or measurements of physiological characteristics of the user (e.g. heart rate, breathing rate, blood pressure, body temperature, etc.). In the first two cases, the status can be determined, for example, by analysing the accelerometer data. In the latter case, it will be appreciated that some additional sensor(s) and/or processing will be provided in order to determine the physiological characteristic measurements (e.g. the heart rate and/or breathing rate can be determined from the accelerometer data).

In the case where the information on the status of the user indicates that there is little or no movement by the user after the detected fall, step 103 can result in an alarm being generated earlier or more quickly than if lots of movement by the user is detected after the fall. In the case where the information on the status of the user indicates that the user has not stood up again following the fall, the alarm can be generated earlier or more quickly than if the user has stood up. In the case where the information on the status of the user comprises measurements of a physiological characteristic of the user, measurements that are abnormal, e.g. that fall outside of an acceptable range or that are above or below a threshold (as appropriate for the physiological characteristic being measured) can result in assistance being obtained more quickly for the user.

In some embodiments the method in FIG. 3 can be performed in the device 2 or system 12, in which case step 101 comprises evaluating the measurements from the accelerometer and any other sensors using the fall detection algorithm, whereas in other embodiments the method can be performed in the system 32 at the remote call centre, in which case step 101 can comprise determining whether a fall signal or alarm signal has been received from the device 2 or system 12.

Figure 4:
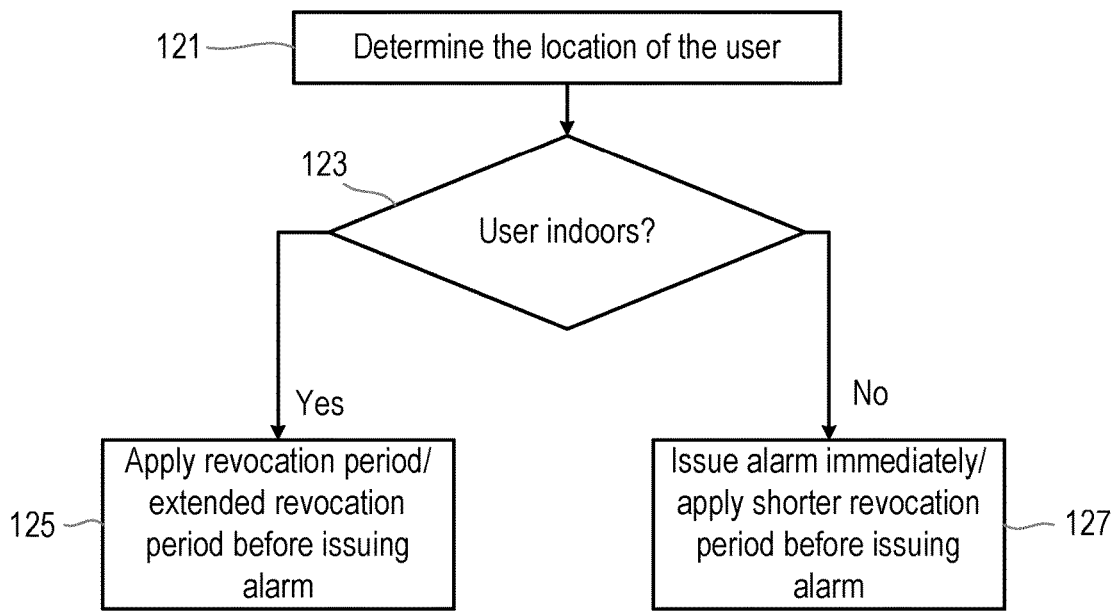
FIG. 4 is a flow chart illustrating a method of determining an action to perform based on the context of the fall according to a first specific embodiment.

FIG. 4 is a flow chart illustrating a method of performing step 103 of FIG. 3 according to a first specific embodiment. In this embodiment, step 103 comprises determining an action to perform based on the context of the fall, and specifically on whether the user is indoors or outdoors when they fell. Thus, in this embodiment, the location of the user is determined (steps 121 and 123). Step 121 can comprise evaluating a location of the user obtained using an SPS receiver or any other location determining means included in the device 2 or system 12. If the user is determined to be indoors, then the action to be taken can be applying a standard revocation period following the detection of a fall to see if the user stands up again (step 125). If the user is determined to be outdoors when they fell, it is possible that they may need assistance more urgently, in which case an alarm signal can be issued immediately to request help for the user straight away (step 127).

Alternatively, instead of issuing an alarm immediately in step 127, a revocation period can be used that is shorter than the revocation period used when the user is indoors.

Figure 5:
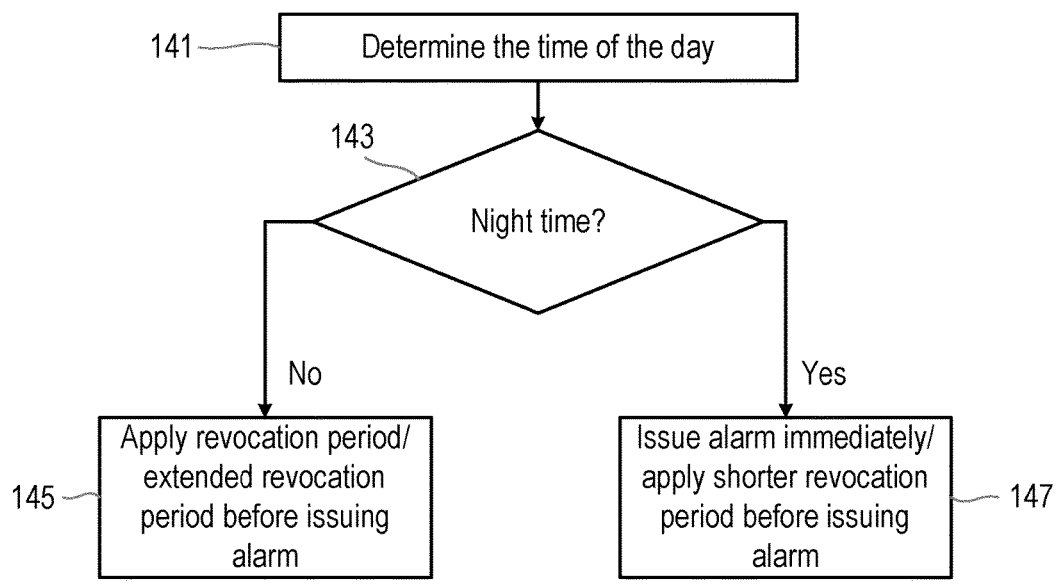
FIG. 5 is a flow chart illustrating a method of determining an action to perform based on the context of the fall according to a second specific embodiment.

FIG. 5 is a flow chart illustrating a method of performing step 103 of FIG. 3 according to a second specific embodiment. In this embodiment, step 103 comprises determining an action to perform based on the context of the fall, and specifically on whether the fall occurred during the day or night. Thus, in this embodiment, the time of the fall is determined (steps 141 and 143). Step 141 can comprise determining the time of the fall and classifying the fall as either occurring during the day or night based on the time. If the fall is determined to have taken place during the day, then the action to be taken can be applying a standard revocation period following the detection of a fall to see if the user stands up again (step 145). If the fall is determined to have taken place at night, it is possible that they may need assistance more urgently, in which case an alarm signal can be issued immediately to request help for the user straight away (step 147).

Alternatively, instead of issuing an alarm immediately in step 147, a revocation period can be used that is shorter than the revocation period used when the user has fallen during the day.

Figure 6:
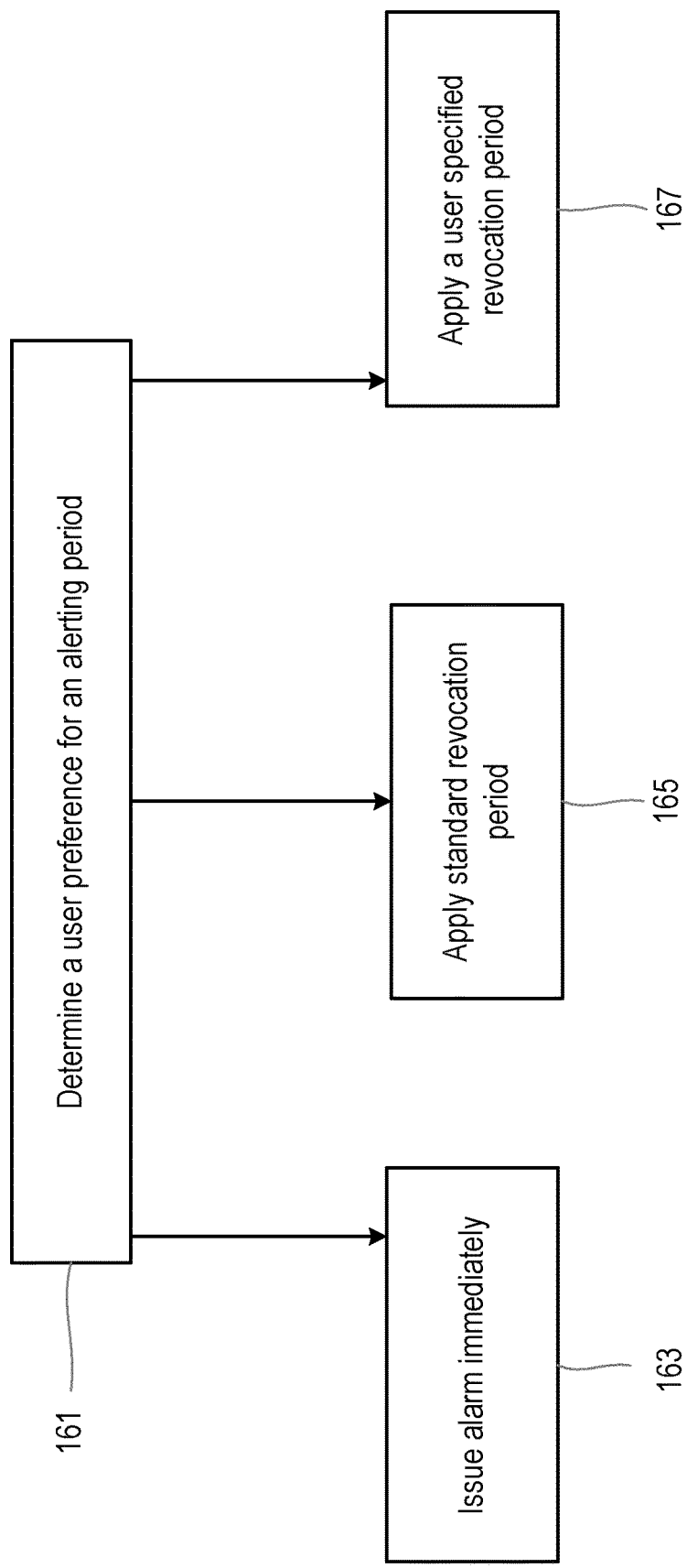
FIG. 6 is a flow chart illustrating a method of determining an action to perform based on a user preference according to a third specific embodiment.

FIG. 6 is a flow chart illustrating a method of performing step 103 based on a user preference according to a third specific embodiment. In this embodiment, step 103 comprises determining an action to perform based on a user preference for an alerting period. Thus, in this embodiment, a user preference is read from a memory 11, 17, 40 (step 161). The method then comprises performing one of steps 163, 165 or 167 based on the user's preference. In particular, an alarm can be issued immediately and assistance obtained straight away (step 163), a standard revocation period can be applied (step 165) or a revocation period of a user-specified length can be applied (step 167).

Figure 7:
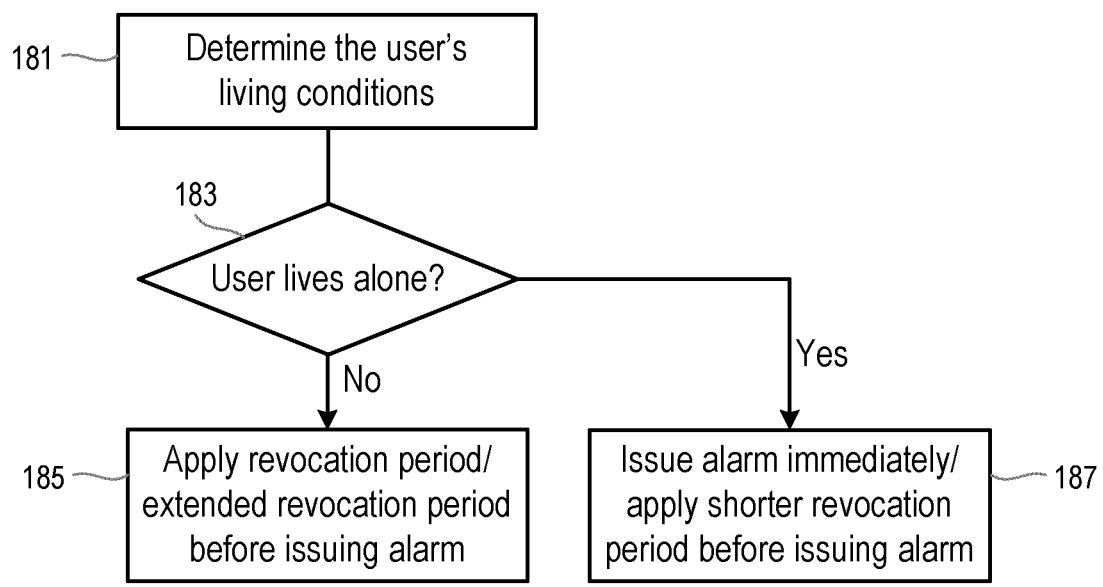
FIG. 7 is a flow chart illustrating a method of determining an action to perform based on a profile of the user according to a fourth specific embodiment.

FIG. 7 is a flow chart illustrating a method of performing step 103 based on a profile of the user according to a fourth specific embodiment. In this embodiment, step 103 comprises determining an action to perform based on the living conditions of the user, and in particular based on whether the user lives alone (steps 181 and 183). If the user does not live alone, there may be people in the vicinity of the user that can assist them in the event that the user has fallen. In that case, if the user profile information indicates that the user does not live alone, the action to be taken can be applying a standard revocation period following the detection of a fall to see if the user stands up again (step 185). If the user profile indicates that the user lives alone, then it is possible that there will not be any assistance immediately available for the user following a fall, in which case an alarm signal can be issued immediately to request help for the user straight away (step 187).

Alternatively, instead of issuing an alarm immediately in step 187, a revocation period can be used that is shorter than the revocation period used when the user lives with someone else.

As noted above, step 103 can comprise determining the action to perform based on multiple ones of the user profile, user preferences and context information. For example, both the location and time of day of the fall can be considered when determining the action to take, with a more urgent action being taken if the fall is determined to have taken place at night, outdoors, or both.

In another example, a user preference for the length of the alerting period can be combined with information on the location of a detected fall to determine the action to take in response to a detected fall. In particular, a user preference can specify that a revocation period should be applied if the fall occurs indoors, and no revocation period should apply if the fall occurs outdoors.

There is therefore provided a method of customising or tailoring the follow-up action taken in response to a detected fall according to a user profile and/or user preference and/or context of the detected fall.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of responding to a detected fall, the method comprising:
   determining which one of two or more actions to perform in response to detecting a fall by a user based on a user profile and/or user preference and/or the context of the detected fall, wherein determining which one of two or more actions to perform includes determining whether to ignore a revocation period and initiate a call or request help for the user instead of waiting for an expiration of the revocation period, or wait for the revocation period to expire before commencing a next action, wherein the determining which one of two or more actions to perform is based on at least the user preference, which comprises an indication of a preset length of the revocation period after the detection of the fall before help is requested for the user or the call is initiated: and performing the determined action; and
   performing the determined action.

2. The method of claim 1, wherein commencing the next action comprises ignoring the detected fall or checking a status of the user after another revocation period.

3. The method of claim 1, wherein the user profile comprises information on whether the user lives alone, the fall risk of the user and/or the fall history of the user.

4. The method of claim 1, wherein the context of the detected fall comprises an indication of when the detected fall occurred, the location of the user when the detected fall occurred, the environmental temperature, the magnitude of a detected impact and/or the direction that the user fell.

5. The method of claim 1, wherein the step of determining further comprises determining which one of two or more actions to perform based on a status of the user following the fall.

6. The method of claim 5, wherein the status of the user comprises an amount of movement by the user following the detected fall, an indication of whether the user has stood up following the detected fall and/or measurements of physiological characteristics.

7. The method of claim 1, wherein the context of the fall indicates whether the fall has occurred indoors or outdoors, and the step of determining further comprises:
   determining whether the detected fall has occurred indoors or outdoors;
   determining that help should be requested for the user or the call initiated if the detected fall is determined to have occurred outdoors; and
   determining that the revocation period should expire before help is requested for the user or the call initiated if the detected fall is determined to have occurred indoors.

8. The method of claim 1, wherein the context of the fall indicates the temperature in the environment in which the detected fall has occurred, and the step of determining further comprises:
   determining whether the temperature in the environment in which the detected fall has occurred is below a threshold;
   determining that help should be requested for the user or the call initiated if the temperature in the environment is below the threshold; and determining that the revocation period should expire before help is requested for the user or the call initiated if the temperature in the environment is above the threshold.

9. The method of claim 1, wherein the step of determining further comprises:
determining whether the user lives alone from the user profile;
determining that help should be requested for the user or the call initiated if the user lives alone; and
determining that the revocation period should expire before help is requested for the user or the call initiated if the user does not live alone.

10. A non-transitory computer readable medium having computer readable code embodied therein, the computer readable code being configured such that, on execution by a processing unit, the processing unit performs the method of:
determining which one of two or more actions to perform in response to detecting a fall by a user based on a user profile and/or user preference and/or the context of the detected fall, wherein determining which one of two or more actions to perform includes determining whether to ignore a revocation period and initiate a call or request help for the user instead of waiting for an expiration of the revocation period, or wait for the revocation period to expire before commencing a next action, wherein the determining which one of two or more actions to perform is based on at least the user preference, which comprises an indication of a preset length of the revocation period after the detection of the fall before help is requested for the user or the call is initiated; and
performing the determined action.

11. An apparatus for providing a response to a detected fall, the apparatus comprising:
a processor unit configured to:
determine which one of two or more actions to perform in response to detecting a fall by a user based on a user profile and/or user preference and/or the context of the detected fall, wherein determining which one of two or more actions to perform includes determining whether to ignore a revocation period and initiate a call or request help for the user instead of waiting for an expiration of the revocation period, or wait for the revocation period to expire before commencing a next action, wherein the determining which one of two or more actions to perform is based on at least the user preference, which comprises an indication of a preset length of the revocation period after the detection of the fall before help is requested for the user or the call is initiated; and
perform the determined action.

12. The apparatus of claim 11, wherein the two or more actions comprise two or more of: ignoring the detected fall, requesting help for the user, initiating a call, waiting for the expiry of a revocation period before requesting help for the user or initiating a call, and checking a status of the user after another revocation period.

13. The apparatus of claim 11, wherein the processing unit is configured to obtain the user profile and/or user preference from a memory.

14. The apparatus of claim 11, wherein the processing unit is configured to obtain information on the context of the detected fall from one or more sensors.

15. The non-transitory computer readable medium of claim 10, the computer readable code being configured such that, on execution by the processing unit, the processing unit further performs the method of commencing the next action by ignoring the detected fall or checking a status of the user after another revocation period.

16. The non-transitory computer readable medium of claim 10, the computer readable code being configured such that, on execution by the processing unit, the processing unit further performs the method of accessing from the user profile information on whether the user lives alone, the fall risk of the user and/or the fall history of the user.

17. The non-transitory computer readable medium of claim 10, the computer readable code being configured such that, on execution by the processing unit, the processing unit further performs the method of determining when the detected fall occurred, the location of the user when the detected fall occurred, the environmental temperature, the magnitude of a detected impact and/or the direction that the user fell.

18. The non-transitory computer readable medium of claim 10, the computer readable code being configured such that, on execution by the processing unit, the processing unit further performs the method of determining which one of two or more actions to perform based on a status of the user following the fall.

* * * * *